United States Patent
Satchivi et al.

(10) Patent No.: US 8,598,084 B2
(45) Date of Patent: Dec. 3, 2013

(54) SYNERGISTIC HERBICIDE/INSECTICIDE COMPOSITION CONTAINING CERTAIN PYRIDINE CARBOXYLIC ACIDS AND CERTAIN INSECTICIDES

(75) Inventors: Norbert M. Satchivi, Westfield, IN (US); Paul R. Schmitzer, Indianapolis, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 10 days.

(21) Appl. No.: 13/029,160

(22) Filed: Feb. 17, 2011

(65) Prior Publication Data

US 2011/0207606 A1    Aug. 25, 2011

Related U.S. Application Data

(60) Provisional application No. 61/306,060, filed on Feb. 19, 2010.

(51) Int. Cl.
| | |
|---|---|
| A01N 63/00 | (2006.01) |
| A01N 43/40 | (2006.01) |
| A01N 25/00 | (2006.01) |
| A01N 53/00 | (2006.01) |
| A01N 37/34 | (2006.01) |
| A01N 57/10 | (2006.01) |
| A01N 37/42 | (2006.01) |
| A01N 43/54 | (2006.01) |
| A01N 41/00 | (2006.01) |
| A01N 51/00 | (2006.01) |

(52) U.S. Cl.
USPC ............ 504/118; 424/405; 504/130; 514/75; 514/79; 514/121; 514/122; 514/156; 514/272; 514/354; 514/355; 514/519; 514/521; 514/531

(58) Field of Classification Search
USPC ............ 504/105, 118, 130; 424/405; 514/75, 514/79, 109, 122, 124, 132, 277, 521, 531, 514/708, 121, 156, 272, 354, 355, 519
See application file for complete search history.

(56) References Cited

U.S. PATENT DOCUMENTS 7,314,849 B2    1/2008 Balko et al.

FOREIGN PATENT DOCUMENTS

| WO | WO2009/029518 A2 | 3/2009 |
|---|---|---|
| WO | 2011/025140 | 2/2011 |

OTHER PUBLICATIONS

LV MCPA/Diflufenican Selective Herbicide. Leaflet. [online]. 4Farmers, 2008 [retrieved on Jul. 20, 2012]. Retrieved from the Internet: <http://www.4farmers.com.au/labels/LV_MCPA_DFF_Leaflet.pdf>, 2 pages.*

Mavrik. Tank Mix Guide [online]. MAUK, 2008 [retrieved on Jul. 20, 2012]. Retrieved from the Internet< http://web.archive.org/web/20080622080433/http://www.mauk.co.uk/tanks.asp?sec=69&con=69> 2 pages.*

* cited by examiner

Primary Examiner — John Pak
Assistant Examiner — Andriae M Holt
(74) Attorney, Agent, or Firm — Robert Chang; Craig E. Mixan

(57) ABSTRACT

An herbicide/insecticide composition containing (a) a pyridine carboxylic acid component and (b) an insecticide component provides synergistic control of selected weeds.

13 Claims, No Drawings

SYNERGISTIC HERBICIDE/INSECTICIDE COMPOSITION CONTAINING CERTAIN PYRIDINE CARBOXYLIC ACIDS AND CERTAIN INSECTICIDES

CROSS REFERENCE TO RELATED APPLICATIONS

This application claims the benefit of U.S. Provisional Patent Application Ser. No. 61/306,060 filed Feb. 19, 2010, which is expressly incorporated by reference herein.

FIELD OF THE INVENTION

This invention concerns a synergistic herbicide/insecticide composition containing (a) an herbicidal pyridine carboxylic acid component and (b) at least one insecticide selected from the group consisting of chlorpyrifos, dimethoate, bifenthrin, cyfluthrin, lambda-cyhalothrin, cypermethrin, deltamethrin, flonicamid, tau-fluvalinate, malathion, pirimicarb and sulfoxaflor.

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Similarly, the protection of crops from insects which destroy or disfigure crops is also a constantly recurring problem in agriculture. To help combat this problem, researchers in the field of synthetic chemistry have produced an extensive variety of chemicals and chemical formulations effective in the control of such insects. Chemical herbicides and insecticides of many types have been disclosed in the literature and a large number are in commercial use.

In some cases, herbicidal active ingredients have been shown to be more effective in combination than when applied individually and this is referred to as "synergism." As described in the *Herbicide Handbook* of the Weed Science Society of America, Eighth Edition, 2002, p. 462, "'synergism' [is] an interaction of two or more factors such that the effect when combined is greater than the predicted effect based on the response to each factor applied separately." The present invention is based on the discovery that certain insecticides and certain pyridine carboxylic acids, already known individually for their insecticidal and herbicidal efficacy, display a synergistic herbicidal effect when applied in combination.

SUMMARY OF THE INVENTION

The present invention concerns a synergistic herbicide/insecticide mixture comprising an herbicidally effective amount of (a) a pyridine carboxylic acid herbicide of the formula (I)

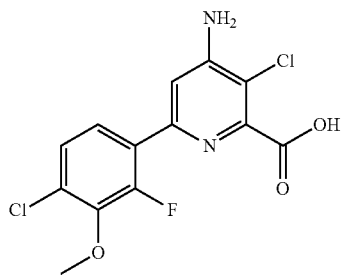

and agriculturally acceptable salts, esters and amides of the carboxylic acid, and (b) an insecticide selected from the group consisting of bifenthrin, chlorpyrifos, cyfluthrin, lambda-cyhalothrin, cypermethrin, deltamethrin, dimethoate, flonicamid, tau-fluvalinate, malathion, pirimicarb and sulfoxaflor. The compositions may also contain an agriculturally acceptable adjuvant or carrier. The synergistic compositions may also generally be employed in combination with known herbicide safeners, particularly with cloquintocet-mexyl.

The present invention also concerns herbicidal/insecticidal compositions for and methods of controlling the growth of undesirable vegetation, particularly in cereals and the use of these synergistic compositions.

4-Amino-3-chloro-6-(4-chloro-2-fluoro-3-methoxyphenyl)pyridine-2-carboxylic acid (I) is used for the control of weeds in cereal crops including spring, winter and durum wheat, and spring and winter barley.

The mixtures of an organophosphate insecticide, such as chlorpyrifos, dimethoate or malathion, and the pyridine carboxylic acid of the formula (I) exhibit a synergistic action in the control of scented mayweed (*Matricaria chamomila* L; MATCH), wild pansy (*Viola tricolor* L; VIOTR), kochia (*Kochia scoparia* L; KCHSC) and Russian thistle (*Salsola iberica* L; SASKR) at application rates lower than the rates of the individual compounds.

It has been surprisingly found that the mixtures of an organophosphate insecticide, such as chlorpyrifos or malathion, and the pyridine carboxylic acid of the formula (I) enhances the phytotoxic effects of the pyridinecarboxylate herbicide of formula (I). It has also unexpectedly found that the use of a herbicide safener such as cloquintocet in composition with a mixture of the pyridinecarboxylate herbicide of the formula (I) and an organophosphate insecticide, such as chlorpyrifos or malathion, exhibits a protecting effect against the phytotoxicity of the mixture of the pyridinecarboxylate herbicide of formula (I) and an organophosphate insecticide on wheat (*Triticum aestivum* L; TRZAS) and barley (*Hordeum vulgare* L; HORVS) without losing the herbicidal effects on weeds such as cleavers (*Galium aparine* L; GALAP), purple deadnettle (*Lamium purpureum* L; LAMPU) and corn poppy (*Papaver rhoeas* L; PAPRH).

It has been surprisingly found that a combination of a pyrethroid insecticide, such as bifenthrin, cyfluthrin, lambda-cyhalothrin, cypermethrin, deltamethrin or tau-fluvalinate, and the pyridine carboxylic acid of the formula (I) exhibits a synergistic action in the control of kochia (*Kochia scoparia* L; KCHSC), scented mayweed (*Matricaria chamomila* L; MATCH), wild pansy (*Viola tricolor* L; VIOTR), redroot pigweed (*Amaranthus retroflexus* L; AMARE), Canada thistle (*Cirsium arvense* L; CIRAR) and bird's-eye speedwell (*Veronica persica* L; VERPE) at application rates lower than the rates of the individual compounds.

It has also been surprisingly found that a mixture of an insecticide, such as flonicamid, and the pyridine carboxylic acid of the formula (I) exhibits a synergistic action in controlling kochia (*Kochia scoparia* L; KCHSC) and scented mayweed (*Matricaria chamomila* L; MATCH) at application rates lower than the rates of the individual compounds.

It has also been surprisingly found that a mixture of a carbamate insecticide, such as pirimicarb, and the pyridine carboxylic acid of the formula (I) exhibits a synergistic action in the control of kochia (*Kochia scoparia* L; KCHSC), scented mayweed (*Matricaria chamomila* L; MATCH), bird's-eye speedwell (*Veronica persica* L; VERPE), wild pansy (*Viola tricolor* L; VIOTR) and Russian thistle (*Salsola iberica* L; SASKR) at application rates lower than the rates of the individual compounds.

It has also been found that the mixture of sulfoxaflor and the pyridine carboxylic acid of the formula (I) shows a synergistic action in control of kochia (*Kochia scoparia* L; KCHSC) and scented mayweed (*Matricaria chamomila* L; MATCH), at application rates lower than the rates of the individual compounds.

DETAILED DESCRIPTION OF THE INVENTION

A number of pyridine carboxylic acid compounds are described in U.S. Pat. No. 7,314,849 (B2), including 4-amino-3-chloro-6-(4-chloro-2-fluoro-3-methoxyphenyl) pyridine-2-carboxylic acid methyl ester (I). The pyridine carboxylic acid of the formula (I) controls annual grass weeds including *Setaria, Pennisetum*, and *Echinochloa*; broadleaf weeds such as *Papaver, Galium, Lamium, Kochia, Amaranthus, Aeschynomene, Sesbania*, and *Monochoria*; and sedge species such as *Cyperus* and *Scirpus*.

Chlorpyrifos is the common name for O,O-diethyl O-(3,5,6-trichloro-2-pyridinyl) phosphorothioate. Its insecticidal activity is described in *The Pesticide Manual*, Fourteenth Edition, 2006. Chlorpyrifos controls Coleoptera, Diptera, Homoptera and Lepidoptera in a wide range of crops.

Dimethoate is the common name for O,O-dimethyl S-[2-(methylamino)-2-oxoethyl]phosphorodithioate. Its insecticidal activity is described in *The Pesticide Manual*, Fourteenth Edition, 2006. Dimethoate controls a wide range of Acari, Aphididae, Aleyrodidae, Coccidae, Coleoptera, Collembola, Diptera, Lepidoptera, Pseudococcidae and Thysanoptera in cereals and other crops, ornamentals and vegetables.

Bifenthrin is the common name for (2-methyl[1,1'-biphenyl]-3-yl)methyl (1R,3R)-rel-3-[(1Z)-2-chloro-3,3,3-trifluoro-1-propenyl]-2,2-dimethylcyclopropanecarboxylate. Its insecticidal activity is described in *The Pesticide Manual*, Fourteenth Edition, 2006. Bifenthrin controls a wide range of foliar pests including Coleoptera and Diptera in cereal crops.

Cyfluthrin is the common name for cyano(4-fluoro-3-phenoxyphenyl)methyl 3-(2,2-dichloroethenyl)-2,2-dimethyl-cyclopropanecarboxylate. Its insecticidal activity is described in *The Pesticide Manual*, Fourteenth Edition, 2006. Cyfluthrin controls a wide range of foliar pests including Coleoptera, Homoptera, Hemiptera and Lepidoptera in cereals, cotton fruit and vegetables.

Lambda-cyhalothrin is the common name for (R)-cyano (3-phenoxyphenyl)methyl (1S,3S)-rel-3-[(1Z)-2-chloro-3,3,3-trifluoro-1-propenyl]-2,2-dimethylcyclopropanecarboxylate. Its insecticidal activity is described in *The Pesticide Manual*, Fourteenth Edition, 2006. Lambda-cyhalothrin controls a wide spectrum of insect pests including aphids, Colorado beetles, thrips, Coleoptera larvae and adults and Lepidoptera larvae in cereals, hops, ornamentals and other crops.

Cypermethrin is the common name for cyano(3-phenoxyphenyl)methyl dichloroethenyl)-2,2-dimethylcyclopropanecarboxylate. Its insecticidal activity is described in *The Pesticide Manual*, Fourteenth Edition, 2006. Cypermethrin controls a wide spectrum of insect pests, including Lepidoptera, Coleoptera, Diptera and Hemiptera in a wide range of crops.

Deltamethrin is the common name (S)-cyano(3-phenoxyphenyl)methyl (1R,3R)-3-(2,2-dibromoethenyl)-2,2-dimethylcyclopropanecarboxylate. Its insecticidal activity is described in *The Pesticide Manual*, Fourteenth Edition, 2006. Deltamethrin controls a wide range of insect pests by contact and ingestion.

Flonicamid is the common name for N-(cyanomethyl)-4-(trifluoromethyl)-3-pyridinecarboxamide. Its insecticidal activity is described in *The Pesticide Manual*, Fourteenth Edition, 2006. Flonicamid controls insect pests, such as aphids and other sucking insects.

Tau-fluvalinate is the common name for cyano(3-phenoxyphenyl)methyl N-[2-chloro-4-(trifluoromethyl)phenyl]-D-valinate. Its insecticidal activity is described in *The Pesticide Manual*, Fourteenth Edition, 2006. Tau-fluvalinate controls a wide range of insect pests including aphids, thrips, leafhoppers, whiteflies in a wide range of crops.

Malathion is the common name for diethyl[(dimethoxythiophosphinothioyl) thio]butanedioate. Its insecticidal activity is described in *The Pesticide Manual*, Fourteenth Edition, 2006. Malathion controls insect pests such as Coleoptera and Lepidoptera in a wide range of crops.

Pirimicarb is the common name for 2-(dimethylamino)-5,6-dimethyl-4-pyrimidinyl dimethylcarbamate. Its insecticidal activity is described in *The Pesticide Manual*, Fourteenth Edition, 2006. Pirimicarb is a selective aphicide used in a wide range of crops.

Sulfoxaflor is the common name for N-[methyloxido[1-[6-(trifluoromethyl)-3-pyridinyl]ethyl]-$\lambda^4$-sulfanylidene]cyanamide. Sulfoxaflor is described in U.S. Pat. No. 7,687,634 B2.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings, plants emerging from vegetative propagules, and established vegetation.

The term insecticide is used herein to mean an active ingredient that kills, controls or otherwise adversely affects the growth of insects. An insecticidally effective amount is an amount of active ingredient which causes an adverse effect to an insect and includes deviations from natural development, killing, regulation, and the like.

Herbicidal activity is exhibited by the compounds of the synergistic mixture when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention postemergence to relatively immature undesirable vegetation to achieve the maximum control of weeds.

In the composition of this invention, the weight ratio of the pyridine carboxylic acid of formula (I) component to the insecticide component at which the herbicidal effect is synergistic lies within the range of between about 35:1 and about 1:1200.

The rate at which the synergistic composition is applied will depend upon the particular type of weed to be controlled, the degree of control required, and the timing and method of application. In general, the composition of the invention can be applied at an application rate of between about 2 grams per hectare (g/ha) and about 1235 g/ha based on the total amount of herbicide and insecticide in the composition. Depending upon the particular insecticide used, the insecticide component is applied at a rate between about 1 g/ha and about 1200 g/ha, the pyridine carboxylic acid of formula (I) component is applied at a rate between about 1 g/ha and about 35 g/ha and the safener component, when used, is applied at a rate between about 0.05 g/ha and about 35 g/ha.

The components of the synergistic mixture of the present invention can be applied either separately or as part of a multipart herbicidal system.

The synergistic mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the synergistic composition of the present invention include: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, orthodichlorobenzene, orthosulfamuron, oryzalin, oxadiargyl, oxadiazon, oxapyrazon, oxasulfuron, oxaziclomefone, oxyfluorfen, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, xylachlor.

The synergistic mixture of the present invention can additionally be employed to control undesirable vegetation in many crops that have been made tolerant to or resistant to them or to other herbicides by genetic manipulation or by mutation and selection. The synergistic composition of the present invention can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. It is generally preferred to use the synergistic composition of the present invention in combination with herbicides that are selective for the crop being treated and which complement the spectrum of weeds controlled by these compounds at the application rate employed. It is further generally preferred to apply the synergistic composition of the present invention and other complementary herbicides at the same time, either as a combination formulation or as a tank mix. Similarly the synergistic mixture of the present invention can be used in conjunction with acetolactate synthase inhibitors on acetolactate synthase inhibitor tolerant crops.

The synergistic composition of the present invention can generally be employed in combination with known herbicide safeners, such as benoxacor, benthiocarb, brassinolide, cloquintocet (mexyl), cyometrinil, cyprosulfamate, daimuron, dichlormid, dicyclonon, dietholate, dimepiperate, disulfoton, fenchlorazole-ethyl, fenclorim, flurazole, fluxofenim, furilazole, harpin proteins, isoxadifen-ethyl, mefenpyr-diethyl, mephenate, MG 191, MON 4660, naphthalic anhydride (NA), oxabetrinil, 829148 and N-phenyl-sulfonylbenzoic acid amides, to enhance their selectivity. Cloquintocet (mexyl) is a particularly preferred safener for the synergistic compositions of the present invention, specifically antagonizing any harmful effect of the synergistic compositions on cereals.

In practice, it is preferable to use the synergistic composition of the present invention in mixtures containing an herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in *McCutcheon's Detergents and Emulsifiers Annual*, MC Publishing Corp., Ridgewood, N.J., 1998, and in *Encyclopedia of Surfactants*, Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

Oftentimes, some of these materials, such as vegetable or seed oils and their esters, can be used interchangeably as an agricultural adjuvant, as a liquid carrier or as a surface active agent.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the synergistic composition of the present invention is generally from 0.001 to 98 percent by weight. Concentrations from 0.01 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before application. The diluted compositions usually applied to weeds or the locus of weeds generally contain 0.0001 to 1 weight percent active ingredient and preferably contain 0.001 to 0.05 weight percent.

The present compositions can be applied to weeds or their locus by the use of conventional ground or aerial dusters, sprayers, and granule applicators, by addition to irrigation or paddy water, and by other conventional means known to those skilled in the art.

The following examples illustrate the present invention.

EXAMPLES

Evaluation of Postemergence Herbicidal Activity of Mixtures in Cereal Crops

Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14 hour (h) photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of an insecticidal compound (as listed in Tables 1 through 18) and the cereal herbicide, 4-amino-3-chloro-6-(4-chloro-2-fluoro-3-methoxyphenyl)pyridine-2-carboxylic acid, alone and in combination. Weighed amounts of esters (methyl) or salts (triethylammonium, TEA) of 4-amino-3-chloro-6-(4-chloro-2-fluoro-3-methoxyphenyl)pyridine-2-carboxylic acid (Compound I) were placed in 25 milliliter (mL) glass vials and dissolved in a volume of 97:3 volume per volume (v/v) acetone/dimethyl sulfoxide (DMSO) to obtain 4.5 milligrams active ingredient per mL (mg ai/mL) concentrated solutions. If Compound I did not dissolve readily, the mixture was warmed and/or sonicated. The concentrated solutions of Compound I were diluted to 1.5 mg ai/mL with the addition of 2 volumes of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio. A dilution solution was prepared by mixing 1 volume of 97:3 v/v acetone/DMSO and 2 volumes of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio. Compound requirements are based upon a 12 mL application volume at a rate of 187 liters per hectare (L/ha). The concentrated solutions of the cereal insecticides were prepared following the same procedure. Weighed amounts of insecticide were placed in 25 milliliter (mL) glass vials and dissolved in a volume of 97:3 v/v acetone/DMSO to obtain concentrated insecticide solutions. The concentrated solutions of the safener were prepared following the same procedure. Weighed amounts of safener were placed in 25 mL glass vials and dissolved in a volume of 97:3 v/v acetone/DMSO to obtain concentrated safener solutions. The concentrated solutions were diluted to 0.75 mg/mL with an aqueous mixture of 1.5% v/v of Agri-dex crop oil concentrate.

Spray solutions of the cereal herbicide and the insecticidal compound mixtures were prepared by adding the concentrated solutions to the appropriate amount of dilution solution to form 12 mL spray solution with active ingredients in combinations. Spray solutions of the cereal herbicide, herbicide safener and the insecticidal compound mixtures were prepared by adding the concentrated solutions to the appropriate amount of dilution solution to form 12 mL spray solution with active ingredients in combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 cm) above average plant canopy. Control plants were sprayed in the same manner with the solvent blank.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. Calculation of the synergistic and antagonistic response of herbicide combinations. *Weeds* 1967, 15, 20-22).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Table 1 through Table 18.

TABLE 1

Synergistic Activity of Compound I and Bifenthrin on Several Key Broadleaf Weeds in Cereal Crops Application rate (g/ha)

| Compound I Methyl ester | Bifenthrin | MATCH Ob | MATCH Ex | SASKR Ob | SASKR Ex | VERPE Ob | VERPE Ex | VIOTR Ob | VIOTR Ex |
|---|---|---|---|---|---|---|---|---|---|
| 8.75 | 0 | 67 | — | 71 | — | 36 | — | 36 | — |
| 17.5 | 0 | 80 | — | 81 | — | 47 | — | 44 | — |
| 35 | 0 | 88 | — | 89 | — | 73 | — | 56 | — |
| 0 | 1.6 | 0 | — | 0 | — | 0 | — | 0 | — |
| 8.75 | 1.6 | 78 | 67 | 91 | 71 | 63 | 36 | 57 | 36 |
| 17.5 | 1.6 | 96 | 80 | 93 | 81 | 72 | 47 | 60 | 44 |
| 35 | 1.6 | 86 | 88 | 91 | 89 | 84 | 73 | 63 | 56 |

TABLE 2

Synergistic Activity of Compound I and Chlorpyrifos on Several Key Broadleaf Weeds in Cereal Crops Application rate (g/ha)

| Compound I Methyl ester | Chlorpyrifos | MATCH Ob | MATCH Ex | SASKR Ob | SASKR Ex | VERPE Ob | VERPE Ex | VIOTR Ob | VIOTR Ex |
|---|---|---|---|---|---|---|---|---|---|
| 8.75 | 0 | 67 | — | 71 | — | 36 | — | 36 | — |
| 17.5 | 0 | 80 | — | 81 | — | 47 | — | 44 | — |
| 35 | 0 | 88 | — | 89 | — | 73 | — | 56 | — |
| 0 | 60 | 0 | — | 0 | — | 0 | — | 0 | — |
| 8.75 | 60 | 80 | 67 | 89 | 71 | 57 | 36 | 70 | 36 |
| 17.5 | 60 | 89 | 80 | 98 | 81 | 73 | 47 | 81 | 44 |
| 35 | 60 | 85 | 88 | 92 | 89 | 73 | 73 | 70 | 56 |

TABLE 3

Synergistic Activity of Compound I and Chlorpyrifos on Several Key Broadleaf Weeds in Cereal Crops Application Rate (g/ha)

| Compound I TEA salt | Chlorpyrifos | SASKR Ob | SASKR Ex | KCHSC Ob | KCHSC Ex | VERPE Ob | VERPE Ex | VIOTR Ob | VIOTR Ex | MATCH Ob | MATCH Ex |
|---|---|---|---|---|---|---|---|---|---|---|---|
| 8.75 | 0 | 80 | | 40 | | 10 | | 23 | | 40 | |
| 17.5 | 0 | 84 | | 55 | | 40 | | 40 | | 67 | |
| 35 | 0 | 86 | | 65 | | 70 | | 47 | | 73 | |
| 0 | 60 | 0 | | 0 | | 0 | | 0 | | 0 | |
| 8.75 | 60 | 85 | 80 | 55 | 40 | 60 | 10 | 63 | 23 | 73 | 40 |
| 17.5 | 60 | 87 | 84 | 67 | 55 | 69 | 40 | 65 | 40 | 82 | 67 |
| 35 | 60 | 90 | 86 | 94 | 65 | 83 | 70 | 63 | 47 | 88 | 73 |

TABLE 4

Synergistic Activity of Compound I and Cyfluthrin on Several Key Broadleaf Weeds in Cereal Crops Application rate (g/ha)

| Compound I Methyl ester | Cyfluthrin | KCHSC Ob | KCHSC Ex | MATCH Ob | MATCH Ex | SASKR Ob | SASKR Ex | VERPE Ob | VERPE Ex | VIOTR Ob | VIOTR Ex |
|---|---|---|---|---|---|---|---|---|---|---|---|
| 8.75 | 0 | 79 | — | 67 | — | 71 | — | 36 | — | 36 | — |
| 17.5 | 0 | 88 | — | 80 | — | 81 | — | 47 | — | 44 | — |
| 35 | 0 | 97 | — | 88 | — | 89 | — | 73 | — | 56 | — |
| 0 | 3.75 | 0 | — | 0 | — | 0 | — | 0 | — | 0 | — |
| 8.75 | 3.75 | 85 | 79 | 75 | 67 | 89 | 71 | 70 | 36 | 52 | 36 |
| 17.5 | 3.75 | 93 | 88 | 93 | 80 | 92 | 81 | 77 | 47 | 62 | 44 |
| 35 | 3.75 | 100 | 97 | 88 | 88 | 93 | 89 | 80 | 73 | 60 | 56 |

TABLE 5

Synergistic Activity of Compound I and lambda-Cyhalothrin on Several Key Broadleaf Weeds in Cereal Crops Application rate (g/ha)

| Compound I Methyl ester | λ-Cyhalothrin | SASKR Ob | SASKR Ex | VERPE Ob | VERPE Ex | VIOTR Ob | VIOTR Ex |
|---|---|---|---|---|---|---|---|
| 8.75 | 0 | 71 | — | 36 | — | 36 | — |
| 17.5 | 0 | 81 | — | 47 | — | 44 | — |
| 35 | 0 | 89 | — | 73 | — | 56 | — |
| 0 | 1.25 | 0 | — | 0 | — | 0 | — |
| 8.75 | 1.25 | 86 | 71 | 72 | 36 | 58 | 36 |
| 17.5 | 1.25 | 92 | 81 | 75 | 47 | 63 | 44 |
| 35 | 1.25 | 93 | 89 | 75 | 73 | 58 | 56 |

TABLE 6

Synergistic Activity of Compound I and Cypermethrin on Several Key Broadleaf Weeds in Cereal Crops

| Application Rate (g/ha) | | KCHSC | | MATCH | | SASKR | | VERPE | | VIOTR | |
|---|---|---|---|---|---|---|---|---|---|---|---|
| Compound I Methyl ester | Cypermethrin | Ob | Ex | Ob | Ex | Ob | Ex | Ob | Ex | Ob | Ex |
| 8.75 | 0 | 79 | — | 67 | — | 71 | — | 36 | — | 36 | — |
| 17.5 | 0 | 88 | — | 80 | — | 81 | — | 47 | — | 44 | — |
| 35 | 0 | 97 | — | 88 | — | 89 | — | 73 | — | 56 | — |
| 8.75 | 6.25 | 82 | 79 | 83 | 67 | 83 | 71 | 80 | 36 | 57 | 36 |
| 17.5 | 6.25 | 92 | 88 | 84 | 80 | 92 | 81 | 83 | 47 | 65 | 44 |
| 35 | 6.25 | 100 | 97 | 86 | 88 | 90 | 89 | 78 | 73 | 62 | 56 |

TABLE 7

Synergistic Activity of Compound I and Deltamethrin on Several Key Broadleaf Weeds in Cereal Crops

| Application rate (g/ha) | | KCHSC | | MATCH | | SASKR | | VERPE | | VIOTR | |
|---|---|---|---|---|---|---|---|---|---|---|---|
| Compound I Methyl ester | Deltamethrin | Ob | Ex | Ob | Ex | Ob | Ex | Ob | Ex | Ob | Ex |
| 8.75 | 0 | 79 | — | 67 | — | 71 | — | 36 | — | 36 | — |
| 17.5 | 0 | 88 | — | 80 | — | 81 | — | 47 | — | 44 | — |
| 35 | 0 | 97 | — | 88 | — | 89 | — | 73 | — | 56 | — |
| 0 | 1.25 | 0 | — | 0 | — | 0 | — | 0 | — | 0 | — |
| 8.75 | 1.25 | 89 | 79 | 82 | 67 | 89 | 71 | 73 | 36 | 57 | 36 |
| 17.5 | 1.25 | 98 | 88 | 82 | 80 | 95 | 81 | 77 | 47 | 63 | 44 |
| 35 | 1.25 | 100 | 97 | 89 | 88 | 92 | 89 | 81 | 73 | 63 | 56 |

TABLE 8

Synergistic Activity of Compound I and Dimethoate on Several Key Broadleaf Weeds in Cereal Crops

| Application rate (g/ha) | | KCHSC | | SASKR | | VERPE | | VIOTR | |
|---|---|---|---|---|---|---|---|---|---|
| Compound I Methyl ester | Dimethoate | Ob | Ex | Ob | Ex | Ob | Ex | Ob | Ex |
| 8.75 | 0 | 79 | — | 71 | — | 36 | — | 36 | — |
| 17.5 | 0 | 88 | — | 81 | — | 47 | — | 44 | — |
| 35 | 0 | 97 | — | 89 | — | 73 | — | 56 | — |
| 0 | 170 | 0 | — | 0 | — | 0 | — | 0 | — |
| 8.75 | 170 | 87 | 79 | 88 | 71 | 72 | 36 | 60 | 36 |
| 17.5 | 170 | 96 | 88 | 93 | 81 | 75 | 47 | 68 | 44 |
| 35 | 170 | 100 | 97 | 92 | 89 | 74 | 73 | 62 | 56 |

TABLE 9

Synergistic Activity of Compound I and Flonicamid on Several Key Broadleaf Weeds in Cereal Crops

| Application rate (g/ha) | | MATCH | | SASKR | | VIOTR | |
|---|---|---|---|---|---|---|---|
| Compound I Methyl ester | Flonicamid | Ob | Ex | Ob | Ex | Ob | Ex |
| 8.75 | 0 | 67 | — | 71 | — | 36 | — |
| 17.5 | 0 | 80 | — | 81 | — | 44 | — |
| 35 | 0 | 88 | — | 89 | — | 56 | — |
| 0 | 17.5 | 0 | — | 0 | — | 0 | — |
| 8.75 | 17.5 | 87 | 67 | 87 | 71 | 43 | 36 |
| 17.5 | 17.5 | 91 | 80 | 91 | 81 | 57 | 44 |
| 35 | 17.5 | 84 | 88 | 93 | 89 | 61 | 56 |

TABLE 10

Synergistic Activity of Compound I and tau-fluvalinate on Several Key Broadleaf Weeds in Cereal Crops

| Application rate (g/ha) | | AMARE | | VIOTR | | CIRAR | |
|---|---|---|---|---|---|---|---|
| Compound I Methyl ester | Tau-fluvalinate | Ob | Ex | Ob | Ex | Ob | Ex |
| 17.5 | 0 | 90 | — | 50 | — | 62 | — |
| 0 | 48 | 0 | — | 0 | — | 0 | — |
| 17.5 | 48 | 97 | 90 | 60 | 50 | 72 | 62 |

TABLE 11

Synergistic Activity of Compound I and Pirimicarb on Several Key Broadleaf Weeds in Cereal Crops

| Application rate (g/ha) | | MATCH | | SASKR | | VERPE | | VIOTR | |
|---|---|---|---|---|---|---|---|---|---|
| Compound I Methyl ester | Pirimicarb | Ob | Ex | Ob | Ex | Ob | Ex | Ob | Ex |
| 8.75 | 0 | 67 | — | 71 | — | 36 | — | 36 | — |
| 17.5 | 0 | 80 | — | 81 | — | 47 | — | 44 | — |
| 35 | 0 | 88 | — | 89 | — | 73 | — | 56 | — |
| 0 | 35 | 0 | — | 0 | — | 0 | — | 0 | — |
| 8.75 | 35 | 79 | 67 | 94 | 71 | 72 | 36 | 62 | 36 |
| 17.5 | 35 | 87 | 80 | 94 | 81 | 83 | 47 | 72 | 44 |
| 35 | 35 | 86 | 88 | 91 | 89 | 73 | 73 | 63 | 56 |

TABLE 12

Synergistic Activity of Compound I and Malathion on Several Key Broadleaf Weeds in Cereal Crops

| Application rate (g/ha) | | KCHSC | | MATCH | | SASKR | | VIOTR | |
|---|---|---|---|---|---|---|---|---|---|
| Compound I Methyl ester | Malathion | Ob | Ex | Ob | Ex | Ob | Ex | Ob | Ex |
| 8.75 | 0 | 79 | — | 67 | — | 71 | — | 36 | — |
| 17.5 | 0 | 88 | — | 80 | — | 81 | — | 44 | — |
| 35 | 0 | 97 | — | 88 | — | 89 | — | 56 | — |
| 0 | 280 | 0 | — | 0 | — | 0 | — | 0 | — |
| 8.75 | 280 | 82 | 79 | 72 | 67 | 87 | 71 | 68 | 36 |
| 17.5 | 280 | 96 | 88 | 87 | 80 | 96 | 81 | 67 | 44 |
| 35 | 280 | 100 | 97 | 88 | 88 | 93 | 89 | 74 | 56 |

TABLE 13

Synergistic Activity of Compound I and Pirimicarb on Several Key Broadleaf Weeds in Cereal Crops

| Application Rate (g/ha) | | SASKR | | KCHSC | | VERPE | | VIOTR | | MATCH | |
|---|---|---|---|---|---|---|---|---|---|---|---|
| Compound I TEA salt | Pirimicarb | Ob | Ex | Ob | Ex | Ob | Ex | Ob | Ex | Ob | Ex |
| 8.75 | 0 | 80 | — | 40 | — | 10 | — | 23 | — | 40 | — |
| 17.5 | 0 | 84 | — | 55 | — | 40 | — | 40 | — | 67 | — |
| 35 | 0 | 86 | — | 65 | — | 70 | — | 47 | — | 73 | — |
| 0 | 35 | 0 | — | 0 | — | 0 | — | 0 | — | 0 | — |
| 8.75 | 35 | 88 | 80 | 57 | 40 | 62 | 10 | 37 | 23 | 80 | 40 |
| 17.5 | 35 | 87 | 84 | 80 | 55 | 82 | 40 | 62 | 40 | 82 | 67 |
| 35 | 35 | 93 | 86 | 98 | 65 | 85 | 70 | 63 | 47 | 94 | 73 |

TABLE 14

Synergistic Activity of Compound I and Sulfoxaflor on Several Key Broadleaf Weeds in Cereal Crops

| Application rate (g/ha) | | MATCH | | SASKR | | VIOTR | |
|---|---|---|---|---|---|---|---|
| Compound I Methyl ester | Sulfoxaflor | Ob | Ex | Ob | Ex | Ob | Ex |
| 8.75 | 0 | 67 | — | 71 | — | 36 | — |
| 17.5 | 0 | 80 | — | 81 | — | 44 | — |
| 35 | 0 | 88 | — | 89 | — | 56 | — |
| 0 | 6.25 | 0 | — | 0 | — | 0 | — |
| 8.75 | 6.25 | 77 | 67 | 92 | 71 | 53 | 36 |
| 17.5 | 6.25 | 83 | 80 | 91 | 81 | 60 | 44 |
| 35 | 6.25 | 94 | 88 | 93 | 89 | 60 | 56 |

TABLE 15

Safening of Synergistic Activity of Compound I and Malathion in Wheat and Barley

| Application Rate (g/ha) | | | TRZAS | | HORVS | | VIOTR | |
|---|---|---|---|---|---|---|---|---|
| Compound I Methyl ester | Cloquintocet | Malathion | Ob | Ex | Ob | Ex | Ob | Ex |
| 35 | 0 | 0 | 39 | | 28 | | 51 | |
| 0 | 2.2 | 0 | 0 | | 0 | | 0 | |
| 0 | 4.375 | 0 | 0 | | 0 | | 0 | |
| 0 | 8.75 | 0 | 0 | | 0 | | 0 | |
| 35 | 2.2 | 0 | 0 | 39 | 0 | 28 | 50 | 51 |
| 35 | 4.375 | 0 | 0 | 39 | 0 | 28 | 31 | 51 |
| 35 | 8.75 | 0 | 0 | 39 | 0 | 28 | 30 | 51 |
| 0 | 0 | 280 | 0 | | 0 | | 0 | |
| 35 | 0 | 280 | 77 | 39 | 75 | 28 | 74 | 51 |
| 35 | 4.375 | 280 | 0 | 39 | 0 | 28 | 69 | 51 |
| 35 | 8.75 | 280 | 0 | 39 | 0 | 28 | 60 | 51 |
| 0 | 0 | 1120 | 0 | | 0 | | 0 | |
| 35 | 0 | 1120 | 72 | 39 | 73 | 28 | 77 | 51 |
| 35 | 2.2 | 1120 | 17 | 39 | 23 | 28 | 70 | 51 |
| 35 | 4.375 | 1120 | 12 | 39 | 27 | 28 | 65 | 51 |
| 35 | 8.75 | 1120 | 12 | 39 | 13 | 28 | 67 | 51 |

TABLE 16

Safening of Synergistic Activity of Compound I and Chlorpyrifos in Wheat and Barley

| Application rate (g/ha) | | | TRZAS | | HORVS | | KCHSC | | MATCH | | SASKR | | VIOTR | |
|---|---|---|---|---|---|---|---|---|---|---|---|---|---|---|
| Compound I Methyl ester | Chlorpyrifos | Cloquintocet | Ob | Ex | Ob | Ex | Ob | Ex | Ob | Ex | Ob | Ex | Ob | Ex |
| 35 | 0 | 0 | 41 | — | 32 | — | 97 | — | 88 | — | 89 | — | 56 | — |
| 35 | 0 | 2.2 | 0 | 41 | 0 | 32 | 100 | 97 | 90 | 88 | 91 | 89 | 50 | 56 |
| 35 | 0 | 4.4 | 0 | 41 | 0 | 32 | 97 | 97 | 92 | 88 | 87 | 89 | 31 | 56 |
| 35 | 0 | 8.75 | 0 | 41 | 0 | 32 | 96 | 97 | 91 | 88 | 88 | 89 | 33 | 56 |
| 35 | 0 | 35 | 0 | 41 | 0 | 32 | 100 | 97 | 81 | 88 | 87 | 89 | 40 | 56 |
| 35 | 240 | 0 | 67 | 41 | 60 | 32 | 100 | 97 | 91 | 88 | 92 | 89 | 68 | 56 |
| 35 | 240 | 2.2 | 5 | 41 | 0 | 32 | 100 | 97 | 95 | 88 | 92 | 89 | 65 | 56 |
| 35 | 240 | 4.4 | 3 | 41 | 0 | 32 | 100 | 97 | 93 | 88 | 92 | 89 | 65 | 56 |
| 35 | 240 | 8.75 | 5 | 41 | 0 | 32 | 100 | 97 | 97 | 88 | 93 | 89 | 62 | 56 |

TABLE 17

Safening of Synergistic Activity of Compound I and Chlorpyrifos in Wheat and Barley

| Application Rate (g/ha) | | | TRZAS | | HORVS | | KCHSC | | SASKR | | VERPE | | VIOTR | |
|---|---|---|---|---|---|---|---|---|---|---|---|---|---|---|
| Compound I Acid | Chlorpyrifos | Cloquintocet | Ob | Ex | Ob | Ex | Ob | Ex | Ob | Ex | Ob | Ex | Ob | Ex |
| 35 | 0 | 0 | 22 | — | 15 | — | 98 | — | 89 | — | 72 | — | 60 | — |
| 0 | 0 | 2.2 | 0 | — | 0 | — | 0 | — | 0 | — | 0 | — | 0 | — |
| 0 | 0 | 4.4 | 0 | — | 0 | — | 0 | — | 0 | — | 0 | — | 0 | — |
| 0 | 0 | 8.75 | 0 | — | 0 | — | 0 | — | 0 | — | 0 | — | 0 | — |
| 35 | 0 | 2.2 | 0 | 22 | 0 | 15 | 100 | 98 | 90 | 89 | 73 | 72 | 57 | 60 |
| 35 | 0 | 4.4 | 0 | 22 | 0 | 15 | 99 | 98 | 91 | 89 | 70 | 72 | 55 | 60 |
| 35 | 0 | 8.75 | 0 | 22 | 0 | 15 | 98 | 98 | 89 | 89 | 77 | 72 | 52 | 60 |
| 0 | 0 | 240 | 0 | — | 0 | — | 0 | — | 0 | — | 0 | — | 0 | — |
| 35 | 240 | 0 | 57 | 22 | 65 | 15 | 98 | 98 | 90 | 89 | 81 | 72 | 75 | 60 |
| 35 | 240 | 2.2 | 8 | 22 | 12 | 15 | 100 | 98 | 91 | 89 | 88 | 72 | 77 | 60 |
| 35 | 240 | 4.4 | 7 | 22 | 13 | 15 | 99 | 98 | 90 | 89 | 87 | 72 | 78 | 60 |
| 35 | 240 | 8.75 | 8 | 22 | 3 | 15 | 100 | 98 | 90 | 89 | 82 | 72 | 73 | 60 |

TABLE 18

Safening of Synergistic Activity of Compound I and Chlorpyrifos in Wheat and Barley

| Application rate (g/ha) | | | TRZAS | | HORVS | | KCHSC | | MATCH | | SASKR | | VIOTR | |
|---|---|---|---|---|---|---|---|---|---|---|---|---|---|---|
| Compound I methyl ester | Malathion | Cloquintocet | Ob | Ex | Ob | Ex | Ob | Ex | Ob | Ex | Ob | Ex | Ob | Ex |
| 35 | 0 | 0 | 41 | — | 32 | — | 97 | — | 88 | — | 89 | — | 56 | — |
| 35 | 0 | 2.2 | 0 | 41 | 0 | 32 | 100 | 97 | 90 | 88 | 91 | 89 | 50 | 56 |
| 35 | 0 | 4.4 | 0 | 41 | 0 | 32 | 97 | 97 | 92 | 88 | 87 | 89 | 31 | 56 |
| 35 | 0 | 8.75 | 0 | 41 | 0 | 32 | 96 | 97 | 91 | 88 | 88 | 89 | 33 | 56 |
| 35 | 0 | 35 | 0 | 41 | 0 | 32 | 100 | 97 | 81 | 88 | 87 | 89 | 40 | 56 |
| 35 | 280 | 0.0 | 77 | 41 | 75 | 32 | 100 | 97 | 88 | 88 | 93 | 89 | 74 | 56 |
| 35 | 280 | 4.4 | 0 | 41 | 0 | 32 | 99 | 97 | 90 | 88 | 94 | 89 | 69 | 56 |
| 35 | 280 | 8.75 | 0 | 41 | 0 | 32 | 100 | 97 | 90 | 88 | 94 | 89 | 60 | 56 |

TRZAS = *Triticum aestivum*, wheat
HORVS = *Hordeum vulgare*, barley
MATCH = *Matricaria chamomila*, scented mayweed
VERPE = *Veronica persica*, bird's-eye speedwell
VIOTR = *Viola tricolor*, wild pansy
KCHSC = *Kochia scoparia*, kochia
SASKR = *Salsola iberica*, Russian thistle
AMARE = *Amaranthus retroflexus*, Redroot pigweed
CIRAR = *Cirsium arvense*, Canada thistle

What is claimed is:

1. A synergistic herbicide/insecticide mixture comprising an herbicidally effective amount of (a) a pyridine carboxylic acid herbicide of the formula

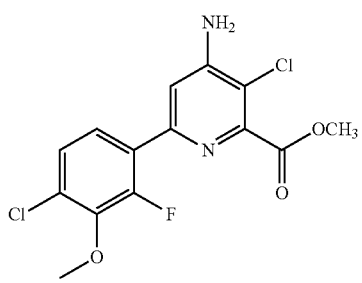

and (b) an insecticide selected from the group consisting of bifenthrin, chlorpyrifos, cyfluthrin, lambda-cyhalothrin, cypermethrin, deltamethrin, dimethoate, flonicamid, tau-fluvalinate, malathion, pirimicarb and sulfoxaflor wherein
when (b) is bifenthrin, the weight ratio of (a) to (b) is from 8.75:1.6 to 35:1.6;
when (b) is chlorpyrifos, the weight ratio of (a) to (b) is from 8.75:60 to 35:60;
when (b) is cyfluthrin, the weight ratio of (a) to (b) is from 8.75:3.75 to 35:3.75;
when (b) is lambda-cyhalothrin, the weight ratio of (a) to (b) is from 7:1 to 28:1;
when (b) is cypermethrin, the weight ratio of (a) to (b) is from 1.4:1 to 5.6:1;
when (b) deltamethrin, the weight ratio of (a) to (b) is from 7:1 to 28:1;
when (b) is dimethoate, the weight ratio of (a) to (b) is from 8.75:170 to 35:170;
when (b) is flonicamid, the weight ratio of (a) to (b) is from 1:2 to 1:0.5;
when (b) is tau-fluvalinate, the weight ratio of (a) to (b) is 17.5:48;
when (b) is pirimicarb, the weight ratio of (a) to (b) is 1:1 to 1:4;
when (b) is malathion, the weight ratio of (a) to (b) is 1:8 to 1:32; and
when (b) is sulfoxaflor, the weight ratio of (a) to (b) is 1.4:1 to 5.6:1.

2. The mixture of claim 1, wherein (b) is chlorpyrifos, and the weight ratio of (a) to (b) is from 8.75:60 to 35:60.

3. The mixture of claim 1, wherein (b) is cyfluthrin, and the weight ratio of (a) to (b) is from 8.75:3.75 to 35:3.75.

4. The mixture of claim 1, wherein (b) is lambda-cyhalothrin, and the weight ratio of (a) to (b) is from 7:1 to 28:1.

5. The mixture of claim 1, wherein (b) is cypermethrin, and the weight ratio of (a) to (b) is from 1.4:1 to 5.6:1.

6. The mixture of claim 1, wherein (b) deltamethrin, and the weight ratio of (a) to (b) is from 7:1 to 28:1.

7. The mixture of claim 1, wherein (b) is dimethoate, and the weight ratio of (a) to (b) is from 8.75:170 to 35:170.

8. The mixture of claim 1, wherein (b) is flonicamid, and the weight ratio of (a) to (b) is from 1:2 to 1:0.5.

9. The mixture of claim 1, wherein (b) is tau-fluvalinate, and the weight ratio of (a) to (b) is 17.5:48.

10. The mixture of claim 1, wherein (b) is pirimicarb, and the weight ratio of (a) to (b) is 1:1 to 1:4.

11. The mixture of claim 1, wherein (b) is malathion, and the weight ratio of (a) to (b) is 1:8 to 1:32.

12. The mixture of claim 1, wherein (b) is sulfoxaflor, and the weight ratio of (a) to (b) is 1.4:1 to 5.6:1.

13. The mixture of claim 1, wherein (b) is bifenthrin, and the weight ratio of (a) to (b) is from 8.75:1.6 to 35:1.6.

* * * * *